United States Patent
Ruben et al.

(10) Patent No.: US 6,963,780 B2
(45) Date of Patent: Nov. 8, 2005

(54) IMPLANTABLE MEDICAL DEVICE INCLUDING A SURFACE-MOUNT TERMINAL ARRAY

(75) Inventors: David A. Ruben, Mesa, AZ (US); Andrew J. Ries, Lino Lakes, MN (US); Juan G. Milla, Mesa, AZ (US); Randy S. Roles, Crystal, MN (US); Terry W. Bruneau, Anoka, MN (US); Steve Craig Warren, Phoenix, AZ (US); David W. Parkin, Phoenix, AZ (US); John V. Anderson, II, Chandler, AZ (US); John K. Day, Chandler, AZ (US); Robert V. Hemann, Jr., Gilbert, AZ (US)

(73) Assignee: Medtronic, Inc., Minneapolis, MN (US)

( * ) Notice: Subject to any disclaimer, the term of this patent is extended or adjusted under 35 U.S.C. 154(b) by 629 days.

(21) Appl. No.: 10/061,718

(22) Filed: Jan. 31, 2002

(65) Prior Publication Data

US 2003/0144707 A1 Jul. 31, 2003

(51) Int. Cl.$^7$ ............................................. A61N 1/375
(52) U.S. Cl. ............................... 607/36; 607/37; 607/9; 607/4; 607/2; 439/626; 429/709; 429/733.1
(58) Field of Search ...................... 607/1–5, 9, 36–38; 439/626, 709, 733.1; 429/709, 733.1

(56) References Cited

U.S. PATENT DOCUMENTS

| | | | |
|---|---|---|---|
| 4,401,120 A | 8/1983 | Hartlaub et al. | 128/419 PT |
| 4,958,632 A | 9/1990 | Duggan | 128/419 PG |
| 5,052,388 A | 10/1991 | Sivula et al. | 128/419 PG |
| 5,080,096 A | 1/1992 | Hooper et al. | 128/419 R |
| 5,088,488 A | 2/1992 | Markowitz et al. | 128/419 PG |
| 5,127,404 A | 7/1992 | Wyborny et al. | 128/419 P |
| 5,154,170 A | 10/1992 | Bennett et al. | 128/419 PG |
| 5,336,246 A * | 8/1994 | Dantanarayana | 607/37 |
| 5,535,097 A | 7/1996 | Ruben et al. | 361/736 |
| 5,749,907 A | 5/1998 | Mann | 607/27 |
| 5,904,708 A | 5/1999 | Goedeke | 607/18 |
| 6,022,322 A | 2/2000 | Prutchi | 600/506 |
| 6,414,835 B1 * | 7/2002 | Wolf et al. | 361/302 |
| 6,459,935 B1 * | 10/2002 | Piersma | 607/37 |
| 6,721,602 B2 * | 4/2004 | Engmark et al. | 607/36 |

FOREIGN PATENT DOCUMENTS

| | | | |
|---|---|---|---|
| EP | 1062982 | 12/2000 | A61N/1/372 |
| WO | WO 0123040 | 4/2001 | A61N/1/365 |

* cited by examiner

*Primary Examiner*—Carl Layno
(74) *Attorney, Agent, or Firm*—Michael C. Soldner; Girma Wolde-Michael

(57) ABSTRACT

An implantable medical device comprises an enclosure, a first plurality of electrical contacts disposed within the enclosure, at least a first electrical component secured within the enclosure, a second plurality of electrical contacts on the first electrical component, and a terminal array for providing electrical coupling between the first and second plurality of electrical contacts. The terminal array comprises a housing having a plurality of apertures therethrough, the housing having a first side and a second opposite side. Each of a plurality of conductive terminals is positioned within one of the plurality of apertures and has a first contact region proximate the first side of the housing and a second contact region proximate the second side of the housing. The first contact region is electrically coupled to one of the first plurality of electrical contacts, and the second contact region is electrically coupled to one of the second plurality of contacts.

16 Claims, 4 Drawing Sheets

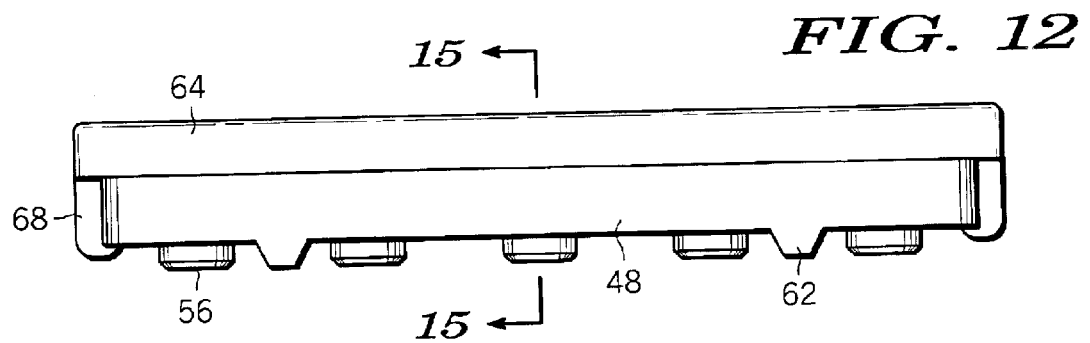
FIG. 12
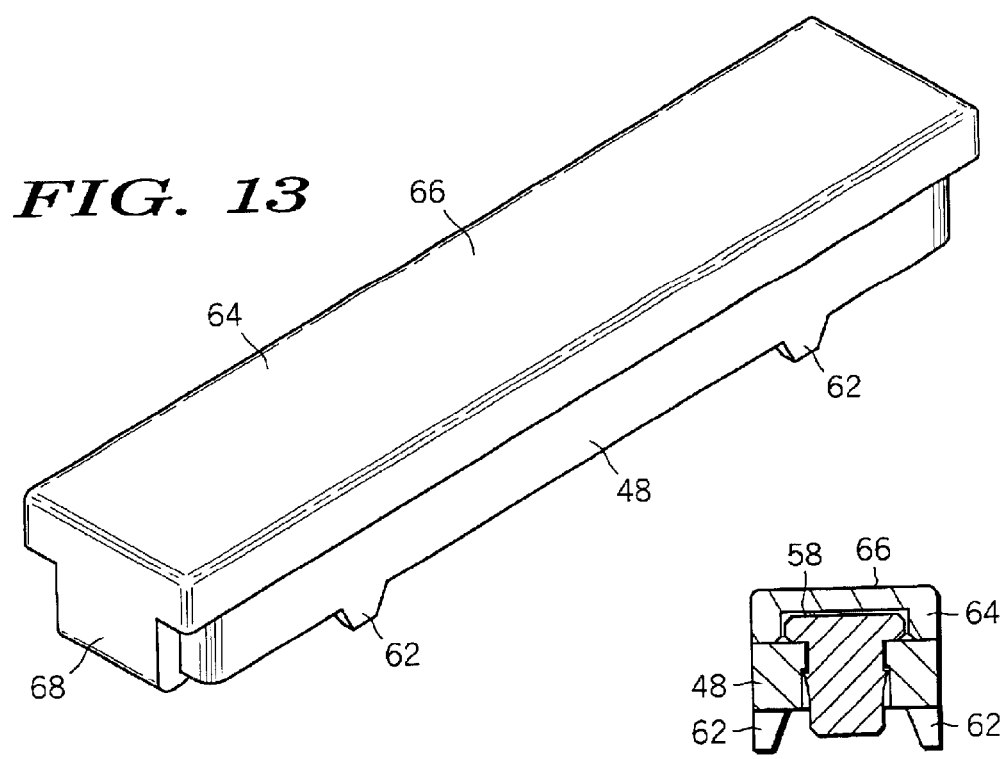
FIG. 13
FIG. 15
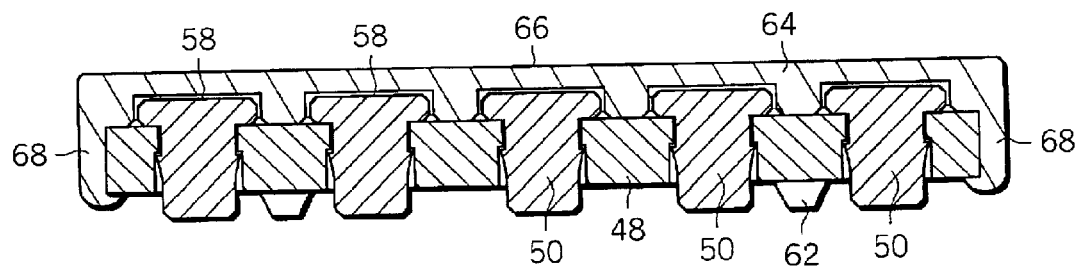
FIG. 14

IMPLANTABLE MEDICAL DEVICE INCLUDING A SURFACE-MOUNT TERMINAL ARRAY

FIELD OF THE INVENTION

This invention relates generally to implantable medical devices, and more particularly to an implantable medical device incorporating a surface-mount solderable terminal array including surfaces suitable for welding and/or wire-bonding.

BACKGROUND OF THE INVENTION

Implantable medical devices such as pacemakers, defibrillators, neuro-stimulators, and the like are generally deployed in a housing comprising two metal halves forming a "clam shell" assembly. Electrical communication to external sensing electrodes and/or therapy delivery electrodes is often accomplished by means of a rigid plastic connecting module fixed to an outer portion of the housing. One or more feed-through connectors permit electrical communication to and from the electrical components or circuitry contained within the housing while at the same time maintaining the hermeticity of the device.

The construction of such implantable medical devices using the above described basic architecture oftentimes requires complex manufacturing operations which increase costs, lower yields, and limit design freedom. One such operation includes providing the electrical contacts and interconnections between components such as batteries, capacitors, and feed-throughs with internally deployed hybrid circuitry formed on substrates such as printed wiring boards (PWBs), flex substrates, ceramic substrates, and the like. That is, the substrates are not directly compatible with welding or wire-bonding. In the case of welding the substrate metalization and even the substrate itself may be damaged due to their respective low melting points. For example, in the case of a PWB or flex substrate, the epoxy glass or polyimide would melt if an attempt were made to weld directly to the plated metal. Ceramic substrates may also be damaged by the rapid local heating. While wire-bonding to the metalization of a PWB or flex circuit is possible, a gold finish is required and solder splatter is possible. Furthermore, the use of a gold finish can cause brittle solder joints.

It is well known that the trend towards smaller device sizes requires smaller and more closely spaced interconnect terminals. Unfortunately, this presents certain problems. First, components can "swim" or "float" on solder pads during the soldering process resulting in non-uniform component spacing and excessive tilting with respect to the PWB surface. This variation must be kept to a minimum to achieve minimum electrical separation and bond/weld variations induced by the angle of their terminal bond/weld surface. Additionally, as the size of the individual terminals or contacts continues to shrink, the terminals are difficult to manage with current pick-and-place surface-mount assembly equipment.

One approach currently being used involves the soldering of individual, gold-plated terminal blocks to the hybrid substrate. Electrical coupling to these blocks is then made by welding or wire-bonding. In addition, the use of individually placed surface-mount solder buttons is known. These approaches, however, still suffer from the above described disadvantages. The use of a ceramic block array provides for multiple connections to a hybrid circuit with consistent terminal spacing and protection from solder wicking to the bond surface; i.e. solder migrating up the side, and in some cases to the top. Unfortunately, the impedance through each terminal from one surface to the other surface results in large voltage drops at high currents.

In view of the forgoing, it should be appreciated that it would be desirable to provide a surface-mount solderable terminal assembly that provides weldable and/or wire bondable surfaces for electrically connecting the components of a hybrid circuit to other components such as batteries, capacitors, feed-throughs, etc. which is cost effective and which provides for reduced spacing between contacts while at the same time avoiding the disadvantages and problems described above. Additional desirable features will become apparent to one skilled in the art from the foregoing background of the invention and following detailed description of a preferred exemplary embodiment and appended claims.

SUMMARY OF THE INVENTION

According to a first aspect of the invention there is provided an implantable medical device which comprises an enclosure, a first plurality of electrical contacts disposed within the enclosure, at least a first electrical component secured within the enclosure, a second plurality of electrical contacts on the first electrical component, and a terminal array for providing electrical coupling between the first and second plurality of electrical contacts. The terminal array comprises a housing having a plurality of apertures therethrough, the housing having a first side and a second opposite side. Each of a plurality of conductive terminals is positioned within one of the plurality of apertures and has a first contact region proximate the first side of the housing and a second contact region proximate the second side of the housing. The first contact region is electrically coupled to one of the first plurality of electrical contacts, and the second contact region is electrically coupled to one of the second plurality of contacts.

BRIEF DESCRIPTION OF THE DRAWINGS

The following drawings are illustrative of particular embodiments and therefore do not limit the scope of the invention but are presented to assist in providing a proper understanding of the invention. The drawings are not to scale (unless so stated) and are intended for use in conjunction with the explanations in the following detailed description. The present invention will hereinafter be described in conjunction with the accompanying drawings, wherein like referenced numerals denote like elements, and;

FIG. 11, FIG. 12 and FIG. 13 are top, side, and isometric views respectively of the inventive surface-mount terminal array equipped with a cover;

FIG. 14 is a cross-sectional view of the terminal array shown in FIG. 11 taken along line 14—14; and FIG. 15 is a cross-sectional view of the terminal array shown in FIG. 12 taken along line 15—15.

DESCRIPTION OF THE PREFFERED EXEMPLARY EMBODIMENTS

Figure 1:
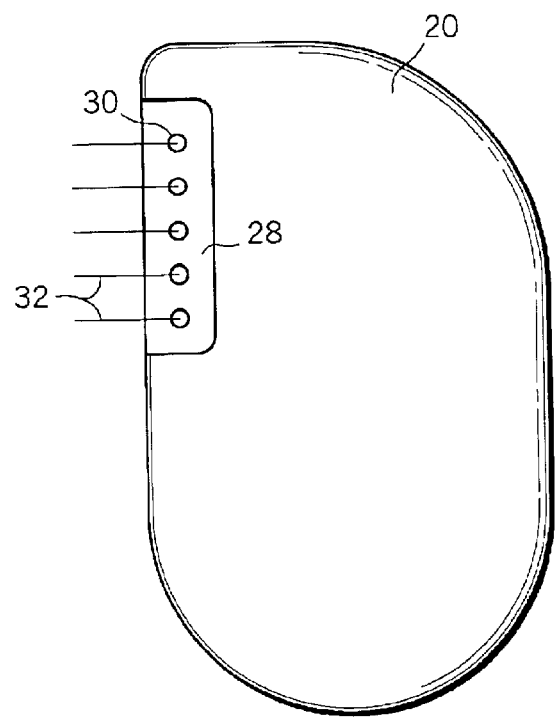
FIG. 1 and FIG. 2 are plan and side views respectively of an assembled implantable medical device.
Figure 2:
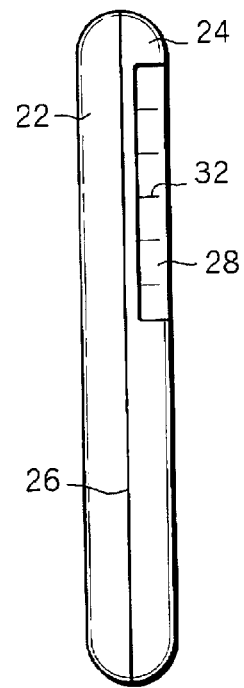

FIG. 1 and FIG. 2 are plan and side views respectively of an implantable medical device in accordance with the present invention. As can be seen, the implantable medical device comprises an enclosure 20 made, for example, of titanium or other suitable biocompatible metal. Enclosure 20 includes first and second halves 22 and 24 respectively which are joined, as for example by welding, along seem 26 to provide a hermetically sealed enclosure which prevents fluid access to the electrical components (e.g. battery, circuitry, etc.) housed within. Enclosure 20 is provided with a recessed area 28 which is equipped with a plurality of feed-throughs 30 from which extend a plurality of leads or feed-through wires 32. Leads 32 are in turn electrically connected via a connecter plug (not shown) to other lead wires which are deployed in an organ which is to be monitored and/or impacted by the implantable medical device. For example, the leads associated with a pacemaker or defibrillator would be deployed in or proximate to heart tissue, and those associated with a nuero-stimulator would be deployed in or near brain tissue.

Figure 3:
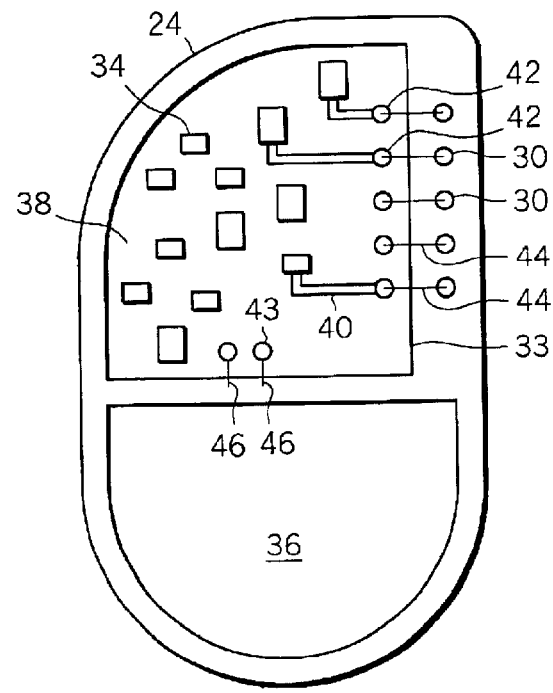
FIG. 3 is a cutaway view of the device shown in FIG. 1.

FIG. 3 is a cutaway view of the implantable medical device shown in FIGS. 1 and 2 revealing certain major components thereof. First and second electrical components 33 and 36 respectively are secured within enclosure half 24 as, for example, by means of an adhesive. An adhesive suitable for this purpose is a two-part epoxy available from Emerson and Cummings located in Woburn, Mass. which combines epoxy 45SC with a catalyst 15SC (Eccobond epoxy). It should be appreciated, however, that other adhesives or securing mechanisms may be employed.

A first electrical component 33 comprises a substrate 34 (e.g. a printed wire board or ceramic substrate) having a plurality of surface-mounted components 38, metalizations 40, a first array of contact pads 42 and a second array of contact pads 43 disposed thereon to form a large scale integrated circuit. For example, in the case of a cardiac pacemaker, the circuit would comprise one or more sense amplifiers, pulse generators, etc. coupled to non-resident heart sensors via contact pads 42, electrical connectors 44 (e.g. wires or conductive ribbons) and feed-throughs 30. It should be clear, however, that the specific circuitry and the function thereof are not to be considered as a limitation since the invention can be employed with circuitry associated with other types of implantable medical devices such as defibrillators, neuro-stimulators, monitors or drug pumps, etc. However, for a further discussion of cardiac pacemakers, the interested reader is directed to U.S. Pat. No. 4,401,120 issued to HARTLAUB et al.; U.S. Pat. No. 4,958,632 issued to DUGGAN; U.S. Pat. No. 5,052,388 issued to SIVULA et al.; U.S. Pat. No. 5,080,096 issued to HOOPER et al.; U.S. Pat. No. 5,088,488 issued to MARKOWITZ et al.; U.S. Pat. No. 5,127,404 issued to WYBORNY et al; U.S. Pat. No. 5,154,170 issued to BENNETT et al.; or U.S. Pat. No. 5,535,097 issued to RUBEN et al.

Electrical component 36 may comprise one or more batteries (in the case of a pacemaker, defibrillator, neurostimulator, etc.), one or more capacitors (in the case of a defibrillator), one or more additional hybrid integrated circuits, or some combination thereof. For the sake of simplicity, however, component 36 will be assumed to be a battery, the positive and negative terminals of which are electrically coupled to contact pads 43 on substrate 34 via electrical conductors 46.

As stated previously, certain problems are encountered when attempts are made to weld (as for example by ultrasonic, resistance, or laser welding) or wire-bond wires or conductive ribbon to contact pads 42 and 43 due to the low melting points of the substrate and/or metalizations connected to the contact pads, possible solder contamination of the site, or heat induced cracking. These problems can be substantially mitigated through the use of a surface-mount terminal shown and described in connection with FIGS. 4–8.

Figure 4:
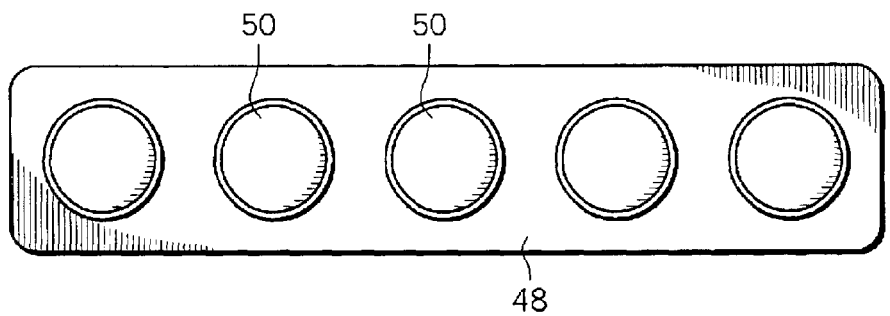
FIG. 4 and FIG. 5 are top and side views respectively of a surface-mount terminal array in accordance with a first embodiment of the present invention.
Figure 5:
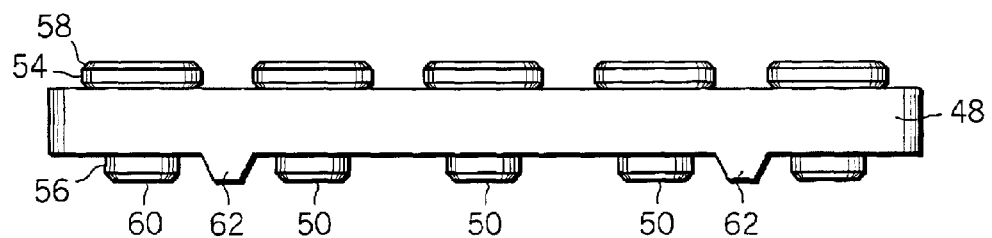

FIG. 4 and FIG. 5 are top and side views of a surface-mount terminal array in accordance with a first embodiment of the present invention. The terminal array comprises a housing 48 and a plurality of conductive terminals 50 extending therethrough. Housing 48 may be manufactured from a moldable material such as a liquid crystal polymer, polysulfone, or other moldable material which provides the required dimensional stability and heat resistance in order to tolerate soldering and welding temperatures. Conductive terminal 50 may be manufactured from nickel, copper, brass, bronze, or other suitable conductive metals. Alternatively, the terminals could be unplated base metal or plated with tin, gold/nickel, palladium/nickel, silver, or other finish. The soldered surface may have a different finish than the welded or wire-bonded surface. This provides for optimum metallization for each joining process. Terminals 50 may be machined with capture features such as the radial protrusion 52 shown in FIG. 10 which enables the terminal to be press-fit into apertures in molded housing 48. Alternatively, terminals 50 may be positioned within the moldable material prior to curing.

Each contact terminal 50 includes a first contact region 54 and a second contact region 56, each of which is provided with flat contact surfaces 58 and 60 respectively. As can be seen, contact region 54 has a larger diameter than that of contact region 60. This not only aids in the positioning of terminal 50 in housing 48, but also provides a larger contact surface so as to facilitate wire-bonding or welding. Finally, support feet 62 maybe provided and/or formed integrally with housing 48 to assist in supporting and positioning the surface-mount terminal array at a desired location on the substrate.

Figure 6:
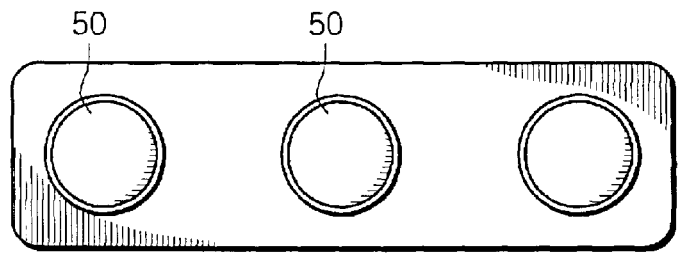
FIG. 6, FIG. 7, and FIG. 8 are top, side and isometric views respectively of a surface-mount terminal array in accordance with a second embodiment of the present invention.
Figure 7:
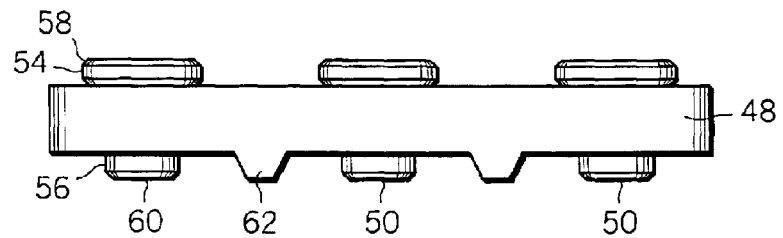
Figure 8:
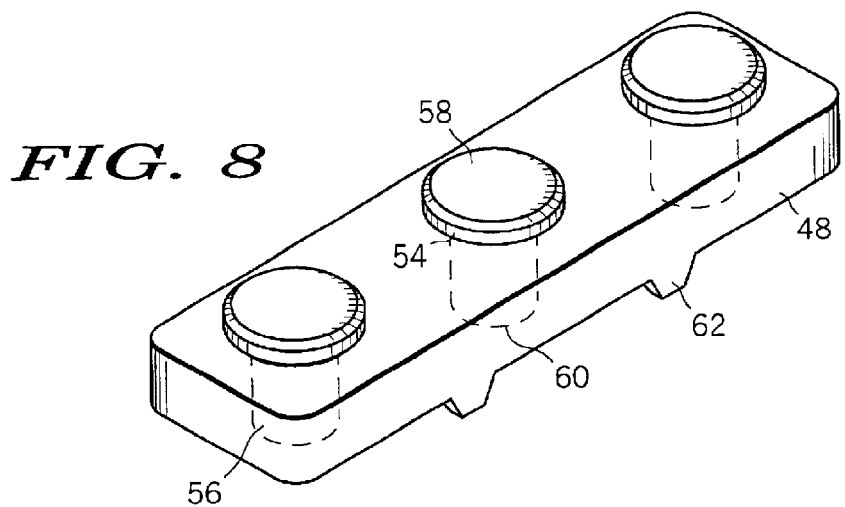
Figure 9:
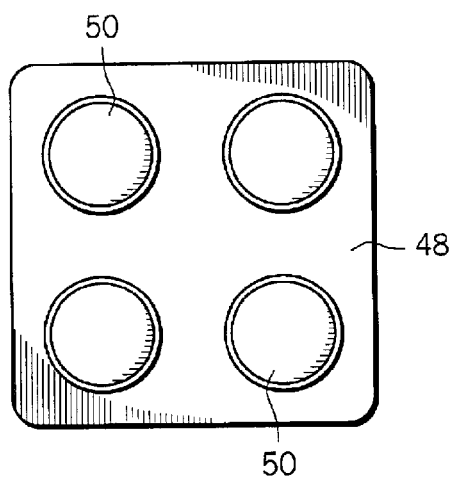
FIG. 9 is a top view of a surface-mount terminal array in accordance with a third embodiment of the present invention.

The inventive terminal array shown in FIGS. 4 and 5 includes a single row of five terminals 50. It should be appreciated, however, that the number of terminals may be varied to suit a particular purpose, and that the terminals may be arranged in one or more rows. For example, FIGS. 6, 7, and 8 are top, side, and isometric views respectively of a surface-mount terminal array in accordance with a second embodiment of the present invention. As can be seen, the device shown in FIGS. 6, 7, and 8 includes only three terminals arranged in a single row. In contrast, FIG. 9 is a top view of a surface-mount terminal array in accordance with a third embodiment of the present invention which comprises four terminals 50 arranged in two rows.

Figure 11:
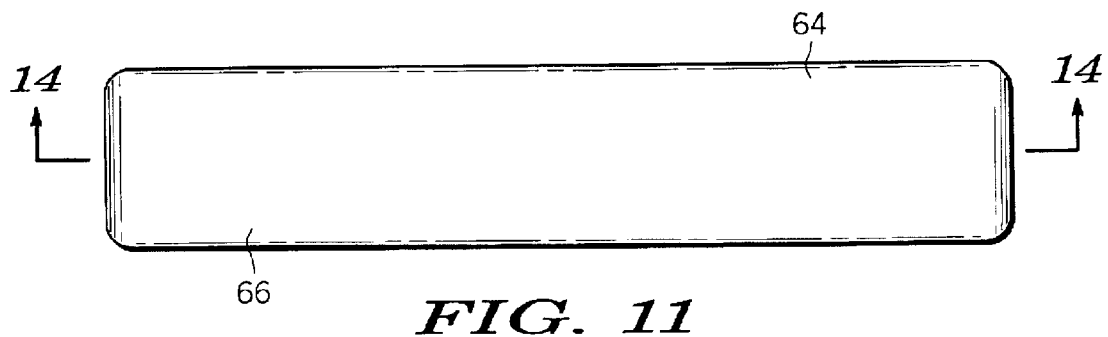

FIG. 11, FIG. 12, and FIG. 13 are top, side, and isometric views respectively of a surface-mount terminal array of the type shown in FIGS. 4 and 5 which is equipped with a removable cap or cover 64. FIGS. 14 and 15 are cross-sectional views of the devices shown in FIGS. 11 and 12 respectively taken along lines 14—14 and 15—15 respectively. Removable cap 64 is provided with a substantially flat surface 66 which facilitates handling and placement. Cap 64 also includes projections 68 which resiliently engage a lower surface of housing 48 to maintain cap 64 in place until deliberately removed. In this manner, the wire-bondable/weldable flat surfaces 58 are protected from solder splatter which avoids the necessity of subsequent time consuming and costly rework. Alternatively, the wire-bondable or weldable surfaces 58 may be coated with a protective material that is readily soluble. Such water-soluble films are commercially available and may be applied by various means including dipping, roller coating, and spraying.

To utilize the inventive surface-mount terminal array, it is first placed on a substrate 34 such that the flat surfaces 60 of contact regions 56 engage contact pads 42 or 43 as the case may be. Due to the physical size of the inventive terminal array, it is easily picked and placed with current automated pick-and-place equipment. Assembly speed is also increased because the multi-terminal array can be placed in roughly the same amount of time as it would take to place a single contact individually.

Figure 10:
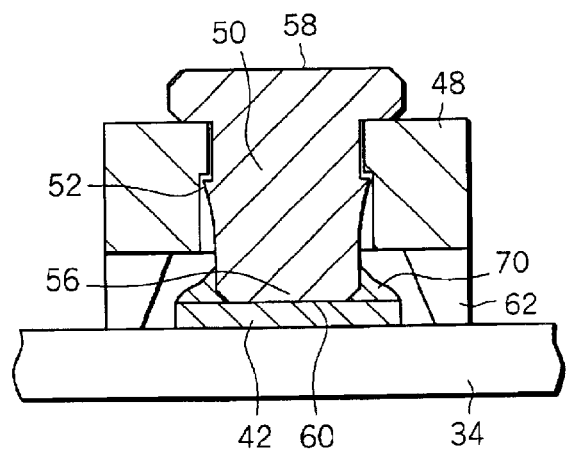
FIG. 10 is a cross-sectional view illustration how one terminal in the inventive terminal array engages a contact pad on a printed wiring board.

Referring to FIG. 10, there is shown a contact terminal 50 having a flat soldering surface 60 which has come to rest on the surface of a contact pad 42 of the type shown in FIG. 3. Contact pad 42 has been preprinted with solder 70 using a solder paste (preferably a eutectic tin-lead or other standard solder) and well known stencil printing techniques. As the hybrid circuit assembly undergoes a soldering process, the solder on contact pad 42 melts and forms a good connection with lower contact region 56 of terminal 50. Thereafter, electrical connections 44 (FIG. 3) may be wire-bonded or welded to upper surface 58 of terminal 50. Since the solder terminal (i.e. contact region 56) is smaller in diameter than wire-bondable or weldable surface 58, it is possible to achieve a complete fillet around contact region 56 without increasing the spacing between adjacent terminals.

Thus, there has been provided a surface-mount terminal array for use in implantable medical devices which provides for reduced spacing between adjacent terminals. Alignment is guaranteed by the design of the contacts and corresponding capture features in the holes into which the terminals are positioned. This maintains all terminals in the array a fixed distance from each other. Due to the improved alignment of the terminals, the demands on the pattern recognition or machine vision equipment during the interconnect process are reduced or eliminated. By raising joining surface 58 above the surface of the substrate to a height of neighboring components, bond head interference is substantially reduced. Various terminal heights may also improve interconnected wire or ribbon looping. Finally, not only does the optional cap provide for easy positioning of the component using convention pick-and-place equipment, the cap also protects the upper surface 58 of terminals 50 from solder splatter during the soldering process.

While preferred exemplary embodiments have been presented in the foregoing detailed description, it should be clear that a vast number of variations in the embodiments exist. For example, while only two contact arrays are shown in FIG. 3, it would not be uncommon to find more than two such arrays.

It should also be appreciated that the preferred embodiments are only examples, and are not intended to limit the scope, applicability, or configuration of the invention in any way. Rather, the foregoing detailed description provides those skilled in the art with a convenient roadmap for implementing the preferred exemplary embodiments of the invention. Various changes may be made in the function and arrangement described connection with the exemplary preferred embodiments without departing from the spirit and scope of the invention as set forth in the appended claims.

What is claimed is:

1. An implantable medical device, comprising:
   an enclosure;
   a first plurality of electrical contacts within said enclosure;
   at least a first electrical component secured within said enclosure;
   a second plurality of electrical contacts on said first electrical component; and
   a terminal array for providing electrical coupling between said first plurality of electrical contacts and said plurality of electrical contacts, said terminal array comprising:
      a housing having a plurality of apertures therethrough, said housing having a first side and a second opposite side; and
      a plurality of conductive terminals, each one positioned within one of side plurality of apertures and having a first contact region proximate said first side and a second contact region proximate second opposite side, said first contact region electrically coupled to one of said first plurality of electrical contacts and said second contact region electrically coupled to one of said second plurality of contacts, wherein said fist electrical component is a first printed wire board and said second plurality of electrical contacts comprises a plurality of contact pads on said first printed wire board, and wherein said plurality of contact pads are presoldered.

2. An implantable medical device according to claim 1 wherein said second contact region is positioned on one of the presoldered contact pads and soldered thereto.

3. An implantable medical device according to claim 2 further comprising a plurality of electrical connectors for coupling each of said first contact regions to one of said first plurality of electrical contacts.

4. An implantable medical device according to claim 3 wherein said plurality of electrical connectors are wire-bonds.

5. An implantable medical device according to claim 3 wherein said plurality of electrical connectors are laser ribbons.

6. An implantable medical device according to claim 3 wherein said first plurality of electrical contacts are feedthroughs in said enclosure.

7. An implantable medical device according to claim 3 wherein said first plurality of electrical contacts are disposed on a second electrical component within said enclosure.

8. An implantable medical device according to claim 7 wherein said second electrical component is a battery.

9. An implantable medical device according to claim 7 wherein said second electrical component is a capacitor.

10. An implantable medical device according to claim 7 wherein said second electrical component is a second printed wire board.

11. An implantable medical device according to claim 7 further comprising a plurality of support feet extending from said second opposite side.

12. An implantable medical device according to claim 7 wherein said first and second contact regions extend beyond said housing.

13. An implantable medical device according to claim 12 wherein each of said plurality of apertures has a first dimension thereacross and wherein said first contact region has a second dimension thereacross which is larger than said first dimension.

14. An implantable medical device according to claim 13 wherein said housing is made of a moldable material.

15. An implantable medical device according to claim 14 wherein said plurality of apertures are arranged in a single row.

16. An implantable medical device according to claim 14 wherein said plurality of apertures are arranged in a plurality of rows.

* * * * *

UNITED STATES PATENT AND TRADEMARK OFFICE
CERTIFICATE OF CORRECTION

PATENT NO.         : 6,963,780 B2                                              Page 1 of 1
APPLICATION NO.    : 10/061718
DATED              : November 8, 2005
INVENTOR(S)        : David A. Ruben et al.

It is certified that error appears in the above-identified patent and that said Letters Patent is hereby corrected as shown below:

Column 6, lines 16 and 17, delete "plurality of" and insert --second plurality of--

Signed and Sealed this

Twenty-sixth Day of December, 2006

JON W. DUDAS
*Director of the United States Patent and Trademark Office*